United States Patent [19]

Klein et al.

[11] 4,247,299
[45] Jan. 27, 1981

[54] NON-CONDUCTIVE POLAR GAS SENSING ELEMENT AND DETECTION SYSTEM

[75] Inventors: Carl F. Klein, Milwaukee; Paul E. Thoma, Burlington, both of Wis.

[73] Assignee: Johnson Controls, Inc., Milwaukee, Wis.

[21] Appl. No.: 916,488

[22] Filed: Jun. 19, 1978

Related U.S. Application Data

[63] Continuation of Ser. No. 702,918, Jul. 6, 1976, abandoned.

[51] Int. Cl.$^3$ .............................................. G01N 27/22
[52] U.S. Cl. ............................ 23/232 E; 324/61 R; 340/629; 340/632; 422/98
[58] Field of Search ..................... 23/23 LE; 422/98; 73/23, 23.1, 25, 26, 27 R, 29, 73, 74; 324/61 R, 65 P; 340/628–630, 632–634; 361/280–286, 289; 427/79; 428/458

[56] References Cited

U.S. PATENT DOCUMENTS

| | | | |
|---|---|---|---|
| 2,462,367 | 2/1949 | De Forrest | 361/281 X |
| 2,806,206 | 9/1957 | Hammond et al. | 324/61 P |
| 2,983,700 | 5/1961 | Rohm | 428/458 |
| 3,054,703 | 9/1962 | Brasure | 428/458 |
| 3,189,802 | 6/1965 | Zisman | 324/32 X |
| 3,247,478 | 4/1966 | Craig | 338/34 |
| 3,252,830 | 5/1966 | Cummin et al. | 427/12 |
| 3,603,954 | 9/1971 | Takeuchi | 422/98 |
| 3,621,377 | 11/1971 | Lim | 361/280 X |
| 3,657,644 | 4/1972 | Beam et al. | 361/282 |
| 3,754,219 | 8/1973 | Klein | 340/628 |
| 3,989,463 | 8/1975 | Klein et al. | 361/280 |

*Primary Examiner*—Michael S. Marcus
*Attorney, Agent, or Firm*—Andrus, Sceales, Starke & Sawall

[57] ABSTRACT

An air pollutant and/or fire combustion sensing apparatus includes a sensing electrode having an electrically non-conductive or dielectric sensing layer which has a surface resistivity in excess of $1 \times 10^{10}$ ohms/square (and preferably $1 \times 10^{15}$), and a bulk resistivity in excess of $1 \times 10^{12}$ ohm-cm, and preferably $1 \times 10^{15}$ at 50% R.H., and which is essentially free of dipole-hydrogen bonding forces such that the surface energy component is primarily due to dispersion bonding forces and, if at all, only incidentally as a result of dipole-hydrogen bonding forces. The latter appears to be a principal factor and desirably has a value of less than 5.0 ergs/cm$^2$ and preferably less than 1.0 erg/cm$^2$. The gases detected have a Van der Waal gas "a" constant and dipole moment. This sensing layer adsorbs air borne polar constituents to alter the charge on the electrode. Optimum results are obtained with polytetrafluoroethylene (Teflon TFE), Perfluoroalkoxy (Teflon PFA), fluorinated ethylene-propylene (Teflon FEP), polystyrene or polyethylene. A high input impedance detecting circuit with good electrometer characteristics responds to the change in the charge, particularly on the surface. A thermally stabilized field effect transistor operating as a voltage amplifier with an input impedance on the order of $10^{10}$ ohms and preferably greater than $10^{12}$ ohms is satisfactory.

17 Claims, 4 Drawing Figures

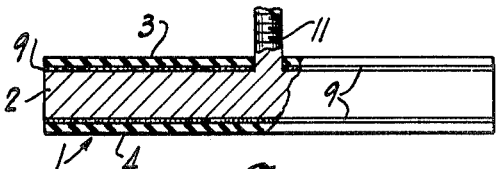
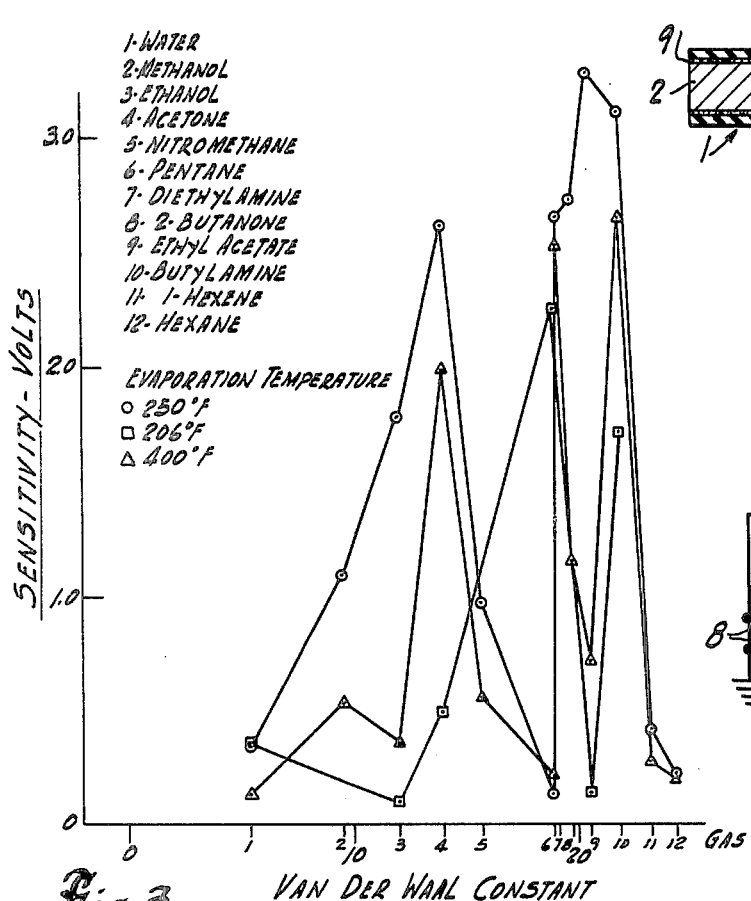
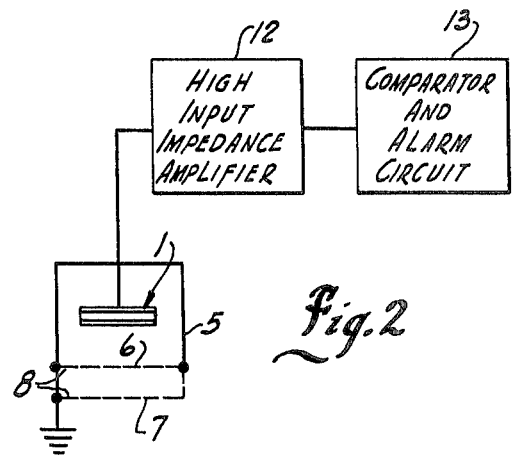
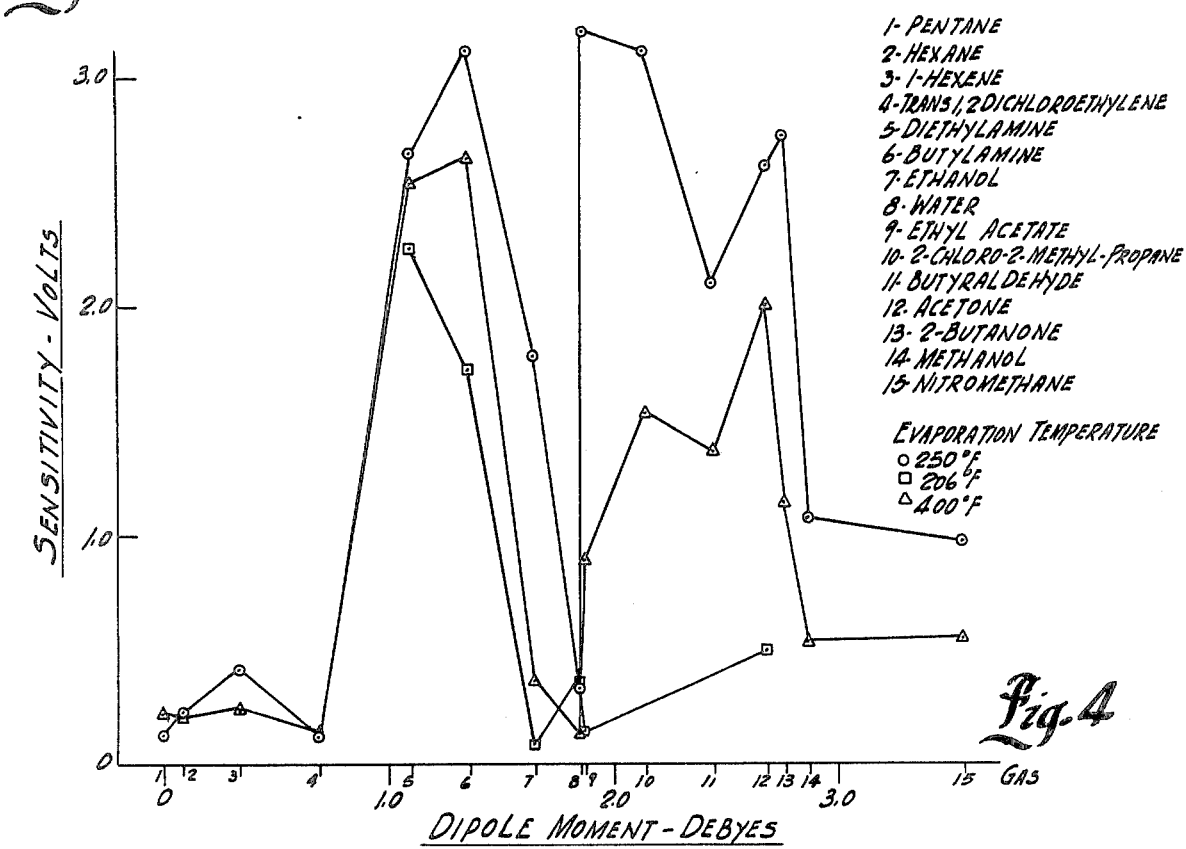

NON-CONDUCTIVE POLAR GAS SENSING ELEMENT AND DETECTION SYSTEM

This is a continuation application, of application, Ser. No. 702,918, filed July 6, 1976 now abandoned.

BACKGROUND OF THE INVENTION

This invention relates to a gaseous product detection system and particularly to an improved sensing element for detecting environmental borne constituents generated as a result of combustion or the like.

Combustion detection and alarm systems employing various sensing and detecting means have been suggested, such as thermal, flame, photo-electric, ionization chamber, semi-conductors of a metal oxide or polymeric organic material, and electrolyte cell sensors. A particularly satisfactory apparatus is disclosed in the copending application of Carl F. Klein et al, Ser. No. 607,892, now U.S. Pat. No. 3,989,463, entitled "Sensing Element and Detection System Employing Such Element for Detection of Environmental Borne Material," and assigned to the same assignee as this application. The system disclosed therein is effective to sense combustion at the initial or incipient stage, as contrasted to the more advanced stage required in the prior art devices employing photo-electric, flame and thermal responses. Thus, as more fully discussed in such applications, the other devices do not react to the invisible combustion gases associated with the incipient stage. Although ionization chamber sensors, which employ radioactive alpha particles sources, capacitance sensing systems, semi-conductor sensing materials, and electrolytic cells have all been suggested to detect initial stages of combustion, they do have special constructional and operational limitations. For example, the National Technical Information Service, Springfield, Virginia 22151 has a paper identified as NASA CR-134693 which particularly discloses semi-conductive polymers which are electronegative as forming charge-transfer complexes with different gases such as in combustion being operable to produce a detectable output. A metal oxide semi-conductor probe is suggested in U.S. Pat. No. 3,603,954 and is commercially marketed. The metal oxide resistance changes to produce a detectable output in the presence of oxidizable gases such as in combustion. However, the metal oxide must be heated and oxidizable gases other than those of combustion may cause false alarms even though a dangerous condition does not exist.

The structure of the above-entitled application provides an improved sensing metal surface which can detect environmental borne products particularly at the incipient stage of combustion. However, the particular sensitive metals and the requirements of fabrication result in a somewhat costly sensor assembly. Further, the degree of sensitivity to certain combustion products may be quite low.

SUMMARY OF THE PRESENT INVENTION

In accordance with the present invention, a sensing element includes a sensitive non-conductive surface which has a surface resistivity in excess of $1 \times 10^{10}$ ohms per square and a bulk resistivity in excess of $1 \times 10^{12}$ ohm -cm and which is essentially free of dipole-hydrogen bonding forces. Preferably, the surface resistivity exceeds $1 \times 10^{15}$ ohms/square and its bulk resistivity exceeds $1 \times 10^{15}$ ohm -cm at 50% R.H. (relative humidity).

More particularly, materials suitable for use in accordance with the teaching of this invention for the detection of gaseous products which have a large Van der Waal gas "a" constant and dipole moment are characterized by a surface energy component due primarily to dispersion bonding forces with a minimum contribution from dipole-hydrogen bonding forces. The minimizing of the component of surface energy due to hydrogen bonding appears as a principal factor responsible for the usefulness of a material in this invention and generally should have a value of less than 5.0 ergs/cm$^2$ and preferably less than 1 erg/cm$^2$. Materials that have been found to provide highly satisfactory results include polytetrafluoroethylene (TFE), perfluoroalkoxy (PFA), fluorinated ethylene-propylene (FEP), which are available under the Teflon trademark of E. I. du Pont de Nemours and Company, polystyrene, and polyethylene, (all of which have a dipole-hydrogen bonding value of less than 1 ergs/cm$^2$). Other suitable materials include polyester (Mylar), Du Pont trademark, polyterephthalate, polyimide, polysulfone and the like. The surface forms part of a free space exposed to the products of combustion at the incipient stage of combustion, and in particular, including the toxic and noxious gases produced by the process of combustion. The detection appears dependent upon the ability of the special element surface to adsorb polar gas molecules generated by combustion, with a resulting induced charge which can be detected. The probe or electrode is also sensitive to ion radicals and charged particles associated with products of combustion and the like which move into close proximity to the surface. Such particles induce an opposite charge on the surface. The adsorption characteristic appears to be a physical attachment or bond between the products and sensing surface. The sensitivity is a function of both the "a" gas constant of the Van der Waal's equation of the state for real gases and the dipole moment of the gaseous molecule. Generally, the invention requires that both values be relatively large.

Although the induced charge creates a more sensitive probe than even created in the above-identified application, the magnitude of the charge is generally such that a high input impedance device which also has good electrometer characteristics is necessary to detect the signal. Generally, a FET (field effect transistor) detecting and amplifying unit provides a highly satisfactory system.

More particularly, a highly practical construction includes a disc-like sensing electrode having a sensing surface of the special dielectric and non-conductive polymer which is preferably adhesively bonded or otherwise intimately secured to a conductive layer. A supporting stud connector is secured to the backside of the electrode and is mounted in a special high bulk and surface resistivity support member to prevent loss of the signals and with an electrical output connection to the stud. An enclosure means including a special shielding member is preferably provided overlying the sensing electrode. The sensing electrode is coupled to a high impedance, high gain signal processing circuitry to provide a compact, integrated detection head.

The present invention has been found to provide an improved highly sensitive surface sensing element formed of relatively inexpensive materials for sensing products of combustion and like environmentally borne products.

BRIEF DESCRIPTION OF THE DRAWING

The drawing furnished herewith illustrates a preferred construction of the present invention in which the above advantages and features are clearly disclosed as well as others which will be clear from the following description of such embodiments.

In the drawing:

FIG. 1 is an elevational view of a sensing electrode or probe having a dielectric sensitive outer layer selected in accordance with the present invention;

FIG. 2 is a block circuit diagram of a fire detection apparatus incorporating a sensing probe of the present invention;

FIG. 3 is a graphical illustration showing the sensitivity of dielectric material to gaseous molecules with different Van der Waal "a" constants; and FIG. 4 is a graphical illustration showing the sensitivity of dielectric material to gaseous molecules with different dipole moments.

DESCRIPTION OF THE ILLUSTRATED EMBODIMENTS

Referring to the drawing and, in particular to FIGS. 1-2, a sensing probe 1 constructed in accordance with the teaching of the present invention is shown including a supporting metal plate 2 and novel sensitive surfaces 3 and 4 on the opposite faces thereof. The surface may, of course, be applied to only one side. The probe 1 may be employed directly but is preferably mounted within an outer supporting housing or case 5 having a pair of cup-shaped perforated plates or electrodes 6 and 7, such as in the previously identified application of the present invention. Perforations 8 in both of the shielding electrodes 6 and 7 permit essentially free access of the surrounding environment into the interior of the electrodes and into contact with the special or probe electrode.

In accordance with the illustrated embodiment of FIG. 1, the probe is a disc-like element including the base metal plate 2 formed of a conducting material and with a special non-conductive and reactive material 3-4, suitably secured, in intimate contact with the opposite faces thereof. The material 3-4 may be deposited as a coating or a film-like material may be secured to the plate 2 by a suitable adhesive 9 such as silicone contact adhesive. Other means may of course be employed. For example, a conductive coat may be vacuum deposited on the reactive material and then mechanically attached to the base plate 2. A supporting post or stud 11 is secured to the plate 2 and suitably supports the probe 1. The probe 1 is connected as the input of a high impedance detection and processing circuit 12 as shown in FIG. 2, and operates a suitable alarm circuit 13 of any suitable construction.

Generally, the probe 1 functions to generate an electrical signal in the presence of gaseous products such as encountered in the incipient and following stages of combustion. By use of an appropriate circuit such signal can be detected. The electronic processing circuit 12 may, of course, be of any suitable construction adapted to provide a high impedance input connection to the probe 1 such as generally disclosed in the inventor's previously identified disclosure and no further illustration or description is given.

Each of the probe coating or layers 3-4 is a special non-conductive material which has special and unique response to the products of combustions including those created during the incipient and initial stages. Layers 3 and 4 may be of the same or different materials. Generally, the gaseous products of combustion include polar gas molecules having a high Van der Waal "a" gas constant. By selection of non-conductive materials which can adsorb such products of combustion an induced charge is created on the sensing probe. The level or magnitude of the induced charge is of course directly related to the polar nature of the gas molecules and their Van der Waal "a" gas constant. The inventors' analysis has found that the combustion products include gas molecules having relatively high dipole moments and which therefore have a polar nature which can produce a highly sensitive response by employing a surface material which promotes the necessary adsorption. Although various dielectrics might be employed, the inventors have found that optimum and particularly practical sensing results when the material is wholly or predominately includes any one or more of materials selected from a group of polymers consisting of polytetrafluoroethylene (TFE), polystyrene, polyethylene, perfluoroalkoxy (PFA) and fluorinated ethylene-propylene (FEP), polyester (Mylar), Dupont trademark, polyterephthalate, polyimide, polysulfone and the like. The characters of the above first three particularly satisfactory and optimum materials are as follows:

| Material | Component of Surface Energy Due to Dispersion Bonding, $\gamma_s^d$ ergs/cm$^2$ | Component of Surface Energy Due to Hydrogen Bonding, $\gamma_s^h$ ergs/cm$^2$ |
| --- | --- | --- |
| TFE | 18.6 | 0.5 |
| Polystyrene | 41.4 | 0.6 |
| Polyethylene | 33.2 | 0.0 |

The minimal surface energy factor due to hydrogen bonding of the materials is an extremely important if not a dominating factor responsible for the usefulness of a material in this invention. Materials with values of $\gamma_s^h$ less than 5.0 ergs/cm$^2$ and preferably less than 1.0 ergs/cm$^2$ are the most useful as the products of combustion sensitive layer in this invention. These materials are characterized by high surface and volume resistivities. Generally, the materials have a surface resistivity on an order greater than $1 \times 10^{10}$ ohms/square and a volume resistivity greater than $1 \times 10^{12}$ ohm cm. Further, the sensitive layer has a very minimum quantity of dipole-hydrogen bonding forces on its surface. The sensor material's sensitivity to combustion products appears to be dependent upon its ability to adsorb polar gas molecules generated during the combustion process. The forces are generally the result of known Van der Waal bonding. A measure of this bonding force is contained in the Van der Waal constant "a" obtained from Van der Waal's equation of state for real gases $(p + a/v^2)(v - b) = RT$. (See Physical Chemistry second edition by Daniels and Alberty, John Wiley, 1961). The magnitude of the probe's sensitivity is therefore related to both its ability to adsorb products of combustion and the polar nature of the adsorbed molecules. FIGS. 3 and 4 show the sensitivity characteristic of a probe formed of any one of the previously identified "Teflon" polymers to a number of gases as a function of the Van der Waal "a" constant of the gas molecule and the dipole moment of such gas, respectively. These characteristics reveal that the Teflon probe senses only gases that have a high dipole moment and therefore can induce a charge on the probe surface and a high Van der Waal "a" constant. Four of the gases (1) 2-butanone, (2) methanol, (3) water, and (4) hexane are shown with different responses particularly discussed for more fully explaining the present invention. The ability of being sensed or not sensed by the Teflon probes is explained by reference to FIGS. 3 and 4. The gas 2-butanone is readily sensed by the probe. This is due to its high dipole moment of 2.76, which is responsible for induction of charge in the Teflon, and its high Van der Waal "a" constant of 19.78, which is responsible for the bonding level. Methanol is sensed comparatively less than 2-butanone even though it has a higher dipole moment (2.87). The lower sensitivity to methanol is due to its lower Van der Waal "a" constant of 9.52. The result is that less methanol is appreciably adsorbed on the surface of the Teflon and consequently the induction of a charge is quite low. The Teflon probe's sensitivity to water is very low, even though water has an appreciable dipole moment (1.87), the Van der Wall "a" constant of water, which is 5.46, is very low. Generally, the inventors have found that gases with a Van der Wall "a" constant below 7 or 8 appear to be poorly sensed by the Teflon probe no matter what their dipole moment is. Hexane has the highest Van der Waal "a" constant (24.39) of the gases evaluated, but it is not sensed by the Teflon probe. The extremely low dipole moment of hexane (0.085) is responsible for this insensitivity because a charge cannot be induced in the Teflon.

The probe is also capable of detecting the ion radicals and charged particles associated with the products of combustion. The gaseous contaminants or combustion aerosols generally possess an electrical charge and when such products are in near proximity to the probe surface, an equal and opposite charge is induced on such surface. The charge transfer from charged combustion products which come in direct contact with the probe, also alter the charge of the surface. Changes in the charge on the electrode's surface also result in a change of potential of the probe and therefore the input to the sensor's high impedance sensing and amplification circuit. The potential is directly proportional to the charge of such ion radicals and charged particles on the sensing electrode's surface.

The adsorption of polar gases on the surface of the sensing element induces a charge in the sensing electrode's surface which is a relatively low level signal. In order to sense this small charge, the detection circuitry must generally include a high input impedance with good electrometer characteristics, such as shown in the previously identified copending application or U.S. Pat. No. 3,754,219. A variety of circuit designs are available for obtaining extremely high input impedance. The four approaches most widely used are use of field effect transistors (FET's), an electrometer tube, a vibrating capacitor, or a varactor bridge. The inventors have found that the field effect transistor is a particularly satisfactory circuit for the input impedance device. Operating as a voltage amplifier an impedance greater than $10^{10}$ ohms and preferably greater than $10^{12}$ ohms is obtained with low offset currents, good voltage and current stability, comparable noise performance, and low power dissipation.

The present invention thus teaches that a highly significant result is obtained by the use of a proper surface of a dielectric material wherein the changes are the direct result of the interaction between the pollutant products and the surface material. In particular, for combustion detection, the inventors have found that the dielectric or non-conductive reactive material suitable for this invention is distinguished from the general class of non-conductive materials by a surface energy component due primarily to dispersion bonding forces with a minimum contribution from dipole-hydrogen bonding forces.

Although shown with the surface material attached to the opposite faces of a plate-like element, other configurations can, of course, be employed. For example, a single side of the support plate may be coated and other than plate-like support members may be readily employed. The important aspect of this invention is the exposure of the gaseous products to a significant surface area of the uniquely selected dielectric material having the special characteristics described in combination with a means to detect the charge characteristic associated with the adsorbed gas molecules. In relatively large areas, a plurality of units may be distributed throughout the area and connected to a signal processing circuit or to individual processing circuits. The present invention thus provides a unique dielectric surface responsive to gaseous products in the surrounding atmosphere such as those created at incipient stages of combustion, and the like. The material and fabrication result in a relatively low cost unit having a long, reliable life. The invention can be employed in any gaseous environment in which the products generated interact with the special surface means to provide a change in the surface charge of the sensing unit.

Various modes of carrying out the invention are contemplated as being within the scope of the following claims particularly pointing out and distinctly claiming the subject matter which is regarded as the invention.

We claim:

1. A method of detecting environmental gaseous products in a gaseous sample comprising contacting a gaseous sample suspected of containing environmental gaseous products with a sensing surface of a dielectric material having a surface resistivity at least equal to $1 \times 10^{10}$ ohms per square and a bulk resistivity of $1 \times 10^{12}$ ohm-cm at 50% relative humidity and having a dispersion bonding forces and minimal dipole hydrogen bonding forces by passing said sample through a free spaced formed by said sensing surface formed by said dielectric material and shield electrode as a reference electrode, holding said shield electrode at a fixed reference potential during the passing of said sample through said free space and thereby reacting said gaseous products with said dielectric material, generating a detectable electrical output potential from said reaction, amplifying said electrical output by passing said output through a high impedance amplifier thereby generating an amplified signal and transmitting said amplified signal to a detecting device for indicating the presence of said gaseous products.

2. The method of claim 1 wherein said surface is formed of dielectric material selected from the group consisting of polytetrafluoroethylene (TFE), perfluoroalkoxy (PFA), fluorinated ethylene propylene (FEP), polystyrene, polyethylene, polyester, polyterephthalate, polyimide and polysulfone.

3. The method of claim 1 wherein said surface is formed of polytetrafluoroethylene (TFE).

4. The method of claim 1 wherein said surface is formed of polystyrene.

5. The method of claim 1 wherein said surface is formed of polyethylene.

6. The method of claim 1 wherein said surface is formed of perfluoroalkoxy (PFA).

7. The method of claim 1 wherein said surface is formed of fluorinated ethylene propylene (FEP).

8. The method of claim 1 wherein said surface is formed of a material including a predominate portion selected from polytetrafluorethylene (TFE), perfluoroalkoxy (PFA), fluorinated ethylene propylene (FEP), polystyrene and polyethylene.

9. The method of claim 1 including the forming of the ground shield as an outer perforated enclosure with said probe means mounted within the enclosure.

10. In the method of claim 1 wherein said dielectric material surface resistivity is in excess of $1 \times 10^{15}$ ohm/square and said bulk resistivity is in excess of $1 \times 10^{15}$ ohm-cm at 50%RH.

11. The method of claim 1 including intimately attaching said material as a coating to a conductive supporting base member.

12. The method of claim 11 including adhesively bonding the dielectric material to the base member.

13. The method of claim 12 including use of a silicone contact adhesive to bond said material to the base member.

14. In the method of claim 1 wherein said dipole-hydrogen bonding force is less than 5.0 ergs/cm$^2$.

15. The method of claim 14 including use of said material having a dipole-hydrogen bonding force of less than 1 ergs/cm$^2$.

16. A method of detecting environmental gaseous products in a gaseous sample comprising contacting a gaseous sample suspected of containing environmental gaseous products such as combustion products with a capacitance sensing surface of a dielectric material selected from the group consisting of polytetrafluoroethylene (TFE), perfluoroalkoxy (PFA), fluorinated ethylene propylene (FEP), polystyrene, and polyethylene by passing said sample through a free spaced formed by said sensing surface formed by said dielectric material and a grounded shield electrode as a capacitance reference electrode spaced to form a sensing capacitor unit, holding said shield electrode at a reference ground potential during the passing of said sample through said free space and thereby reacting said gaseous products with said dielectric material, generating a detectable electrical output potential from said reaction, amplifying said electrical output by passing said output through a high impedance amplifier thereby generating an amplified signal and transmitting said amplified signal to a detecting device for indicating the presence of said gaseous products.

17. The method of claim 16 including forming of the probe means as a disc-like element mounted within the ground shield means and having said material on opposite sides of the first electrode means.

* * * * *